United States Patent
Kashmirian

(10) Patent No.: US 9,962,116 B2
(45) Date of Patent: May 8, 2018

(54) SAMPLING DEVICE

(71) Applicant: ikashmore Pty Ltd., Kambah, Australian Capital Territory (AU)

(72) Inventor: Avtar Kashmirian, Kambah (AU)

(73) Assignee: IKASHMORE PTY LTD, Kambah, Australian Capital Territory (AU)

( * ) Notice: Subject to any disclaimer, the term of this patent is extended or adjusted under 35 U.S.C. 154(b) by 393 days.

(21) Appl. No.: 14/877,760

(22) Filed: Oct. 7, 2015

(65) Prior Publication Data

US 2016/0100784 A1    Apr. 14, 2016

(30) Foreign Application Priority Data

Oct. 10, 2014  (AU) .............................. 2014904055

(51) Int. Cl.
*A61B 5/15*     (2006.01)
*A61B 5/154*    (2006.01)

(52) U.S. Cl.
CPC .......... *A61B 5/15003* (2013.01); *A61B 5/154* (2013.01); *A61B 5/150351* (2013.01); *A61B 5/150648* (2013.01); *A61B 5/150732* (2013.01); *A61B 5/150389* (2013.01); *A61B 5/150473* (2013.01)

(58) Field of Classification Search
CPC ..... A61B 5/15003; A61B 5/351; A61B 5/648; A61B 5/732; A61B 5/473
See application file for complete search history.

(56) References Cited

U.S. PATENT DOCUMENTS 5,120,311 A * 6/1992 Sagstetter .......... A61B 5/15003
                                                     600/576
6,648,835 B1 * 11/2003 Shemesh ............ A61B 5/15003
                                                     600/573

FOREIGN PATENT DOCUMENTS

WO         00/49939 A1     8/2000
WO      2011/140596 A1    11/2011
WO   WO 2011140596 A1 *   11/2011  ............ A61J 1/2096

OTHER PUBLICATIONS

UK Patent Office Search Report (Appln. No. GB1517714.0); Date of Search: Mar. 15, 2016.

* cited by examiner

*Primary Examiner* — Michael C Stout
*Assistant Examiner* — Nicholas E Kolderman
(74) *Attorney, Agent, or Firm* — Howard & Howard Attorneys PLLC

(57) ABSTRACT

A sampling device for a sampling container. A pair of elongate flexible arms extend from a side wall away from a bottom end. The arms being oppositely located across a base chamber. A lower member has a flange and an aperture. A collar extends from the flange and is adapted to retain an end of a spring. An elongate cover has a first end and a second end. The first end being adapted in use to connect to a base and the second end being adapted in use to connect to an upper member. The upper and lower members are adapted to move along the axis by the positioning of a sampling container in the sampling chamber and the application of a force towards a base, permits a needle or blood bag tube located within a connector to discharge liquid into a sampling container.

10 Claims, 14 Drawing Sheets

SAMPLING DEVICE

CROSS-REFERENCE TO RELATED APPLICATION

This application claims priority to Australian Patent Application No. 2014904055, filed Oct. 10, 2014, the disclosure of which is hereby incorporated by reference in its entirety.

TECHNICAL FIELD

The present invention relates to a sampling device and in particular to a device or adapter to facilitate the safe sampling of liquids from a needle or other such elongated tubular injection device.

BACKGROUND ART

It has become common throughout the world to take samples of liquids from various locations, such as blood in a human for example, to allow researchers, doctors, medical technicians or the like to conduct testing of those samples. In the past, such testing has involved the use of an injection device such as a needle, withdrawing a sample of the liquid from a location or reservoir (such as the arm of a person) and expelling some of that liquid into a sampling container such as a bottle, vial, test tube, or the like. Due to the nature of such operations, the doctor, researcher or medical technician can inflict a needle stick injury on themselves or others. This can be compounded by the transference of blood, viruses and other materials.

To alleviate this, larger, safer injectors were created. However, such devices are excessively complicated, difficult to manufacture and very expensive to produce which greatly inhibits their use as it is common for locations where a large amount of sampling occurs such as blood banks, hospitals, universities or the like, to utilise a large number of needles. By utilising cheaper, simpler needles, with a sampling device or adapter fitted between the needle and the sampling container, needle stick injuries and transference could be reduced. It has however been found that such sampling devices have not been sufficiently engineered, are not tamper proof and still cause needle stick injuries and transference. Further, such devices are often complicated, can break easily and are too expensive. Accordingly, there is a need for a better sampling device/adapter which prevents needle stick injuries and transference occurring, whilst also being of simple construction, easy to manufacture and inexpensive.

It is an object of the present invention to substantially overcome or at least ameliorate one or more of the disadvantages of the prior art, or to at least provide a useful alternative.

SUMMARY OF INVENTION

There is disclosed herein a sampling device adapted to connect in use a needle or blood bag tube with a sampling container; said device including a base having a bottom end, a side wall extending away from said bottom end to a rim to define a base chamber, a pair of elongate flexible arms extending from said side wall away from said bottom end, said arms being oppositely located across said base chamber, an elongate boss located within said base chamber and extending away from said bottom end, said boss having an aperture defining a longitudinal axis;

a spring adapted in use to be located at least partly within said chamber, about said boss and extending away from said bottom end;

a lower member having a flange and an aperture, a collar extending from said flange and adapted to retain an end of said spring, and at least one leg extending away from said flange opposite to said collar;

an upper member having a flange in use operatively associated with the flange of said lower member, said flange having an aperture corresponding with said aperture of said lower member, a boss extending about said aperture and away from said flange, a wall extending away from said flange to a rim to define a sampling chamber; at least one slot adapted in use to receive the at least one leg of said lower member in use;

an elongate cover having a first end and a second end, said first end being adapted in use to connect to said base and said second end being adapted in use to connect to said upper member;

a connector operatively associated with said boss of said base and having an elongate tube adapted to extend along said axis;

whereby in use, said upper and lower members are adapted to move along said axis by the positioning of a sampling container in said sampling chamber and the application of a force towards said base, upon movement of said upper member, an end of said tube of said connector extends beyond said boss of said upper member permitting a needle or blood bag tube located within said connector to discharge liquid into said sampling container.

Preferably, said arms of said base have a locking member adapted to engage and disengage said lower member in use to permit movement of said upper and lower members along said axis.

Preferably, said locking member includes a flexible portion having a step, the step adapted to contact said flange of said lower member, upon application of said force said step being moved out of engagement with said lower member and towards said cover.

Preferably, said boss of said base includes a connecting section, at least a portion of said connector having a corresponding connecting section to secure said connector to said boss.

Preferably, said connecting sections include threads.

Preferably, said connector includes a luer.

Preferably, said base includes a retainer extending from said bottom end and adapted to retain an end of said spring.

Preferably, said lower member includes four legs and said upper member includes four corresponding apertures.

Preferably, said rim of said base includes a step adapted in use to connect with a corresponding step in said first end of said cover.

Preferably, said second end of said cover includes a lip extending towards said axis and adapted to connect with said rim of said upper member.

BRIEF DESCRIPTION OF DRAWINGS

A preferred form of the present invention will now be described, by way of example only, with reference to the accompanying drawings, wherein.

DESCRIPTION OF EMBODIMENTS

Figure 1:
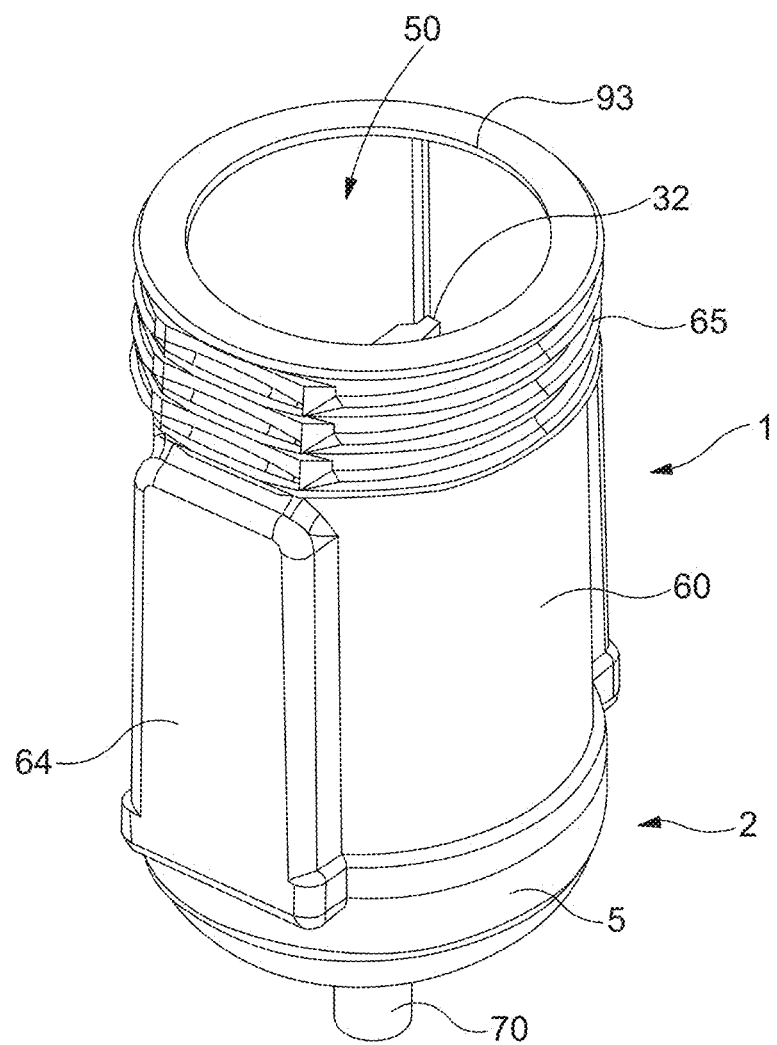
FIG. 1 is a perspective view of a sampling device of an embodiment of the present invention.
Figure 2:
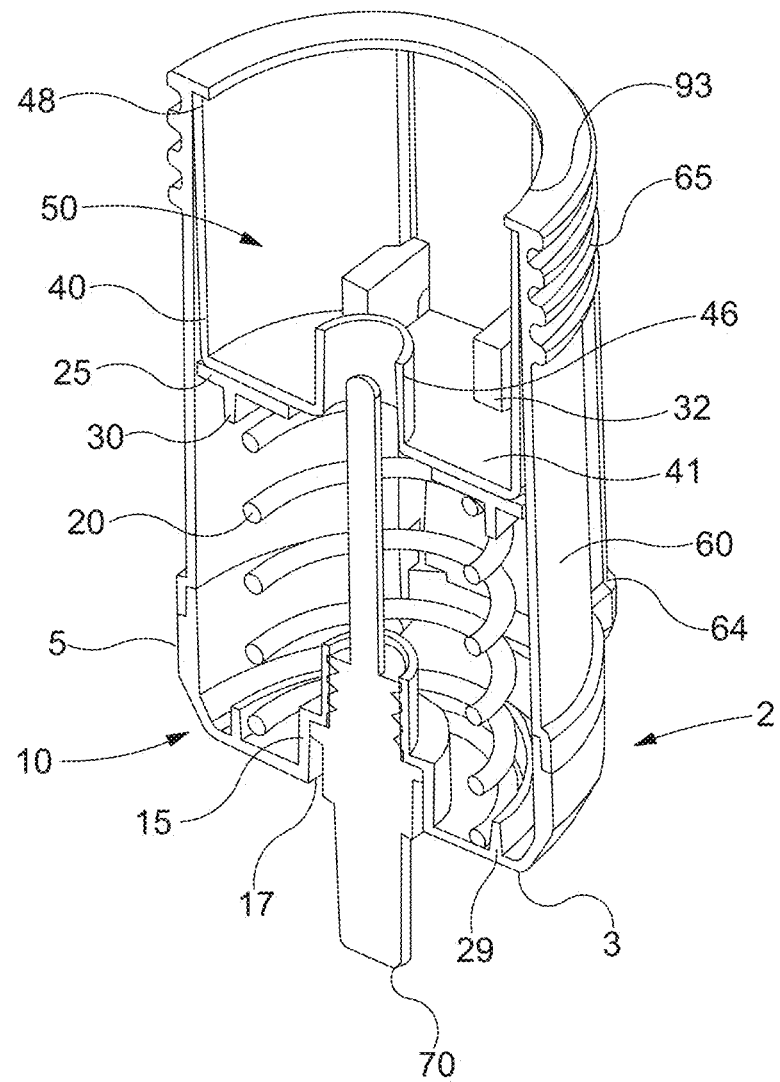
FIG. 2 is a cross-sectional view of FIG. 1 showing the device in an expanded position.
Figure 9:
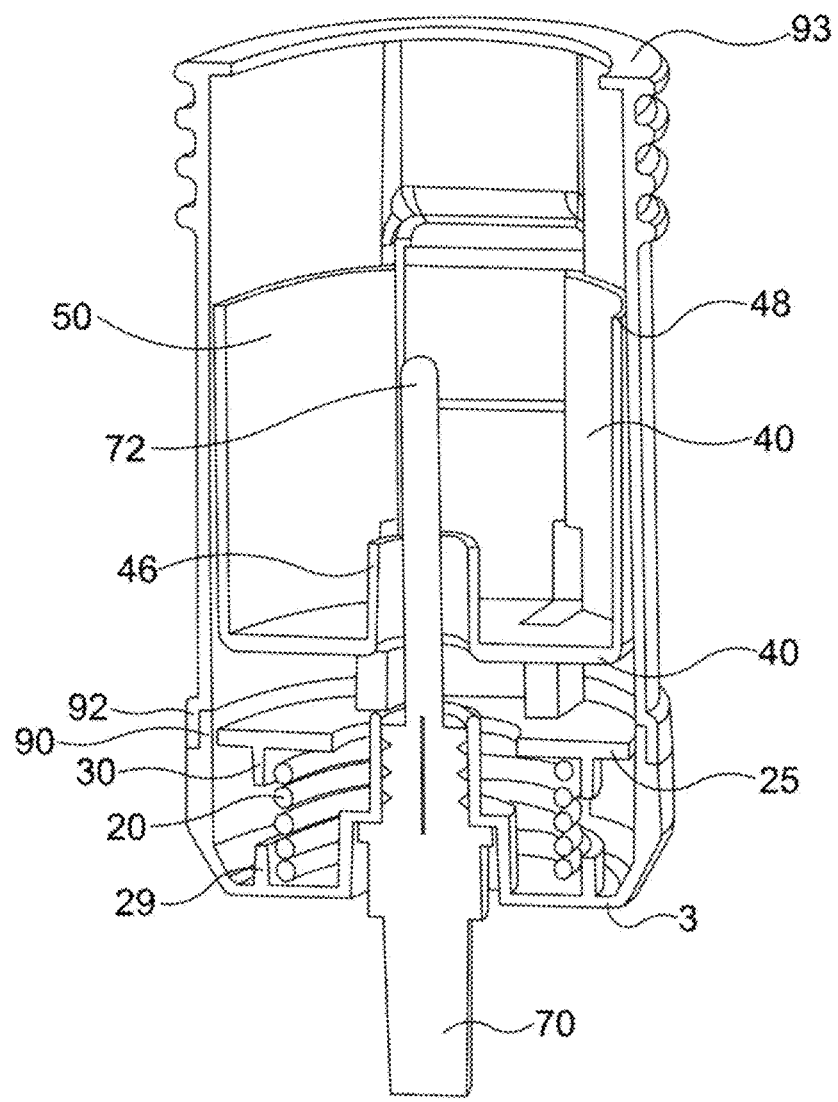
FIG. 9 is a rotated cross-sectional view of FIG. 1 showing the device in a depressed position.
Figure 10:
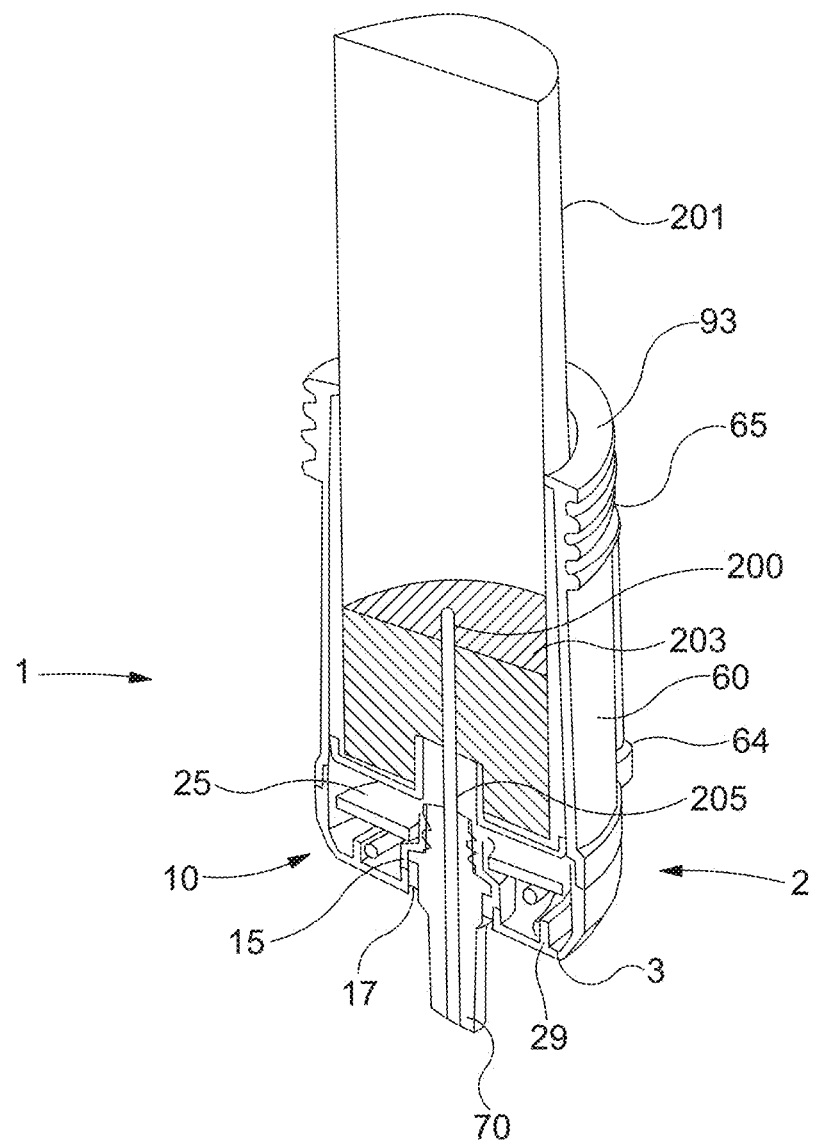
FIG. 10 is a cross-sectional view showing a needle and container in situ.

In the drawings and as best seen in FIG. 10, there is disclosed a preferred embodiment of the present invention including a sampling device or adapter 1 adapted to connect a needle 200 with a sampling container 201. FIG. 2 shows the device 1 in an expanded or ready to use position and FIG. 9 shows the device 1 in a depressed or used position. The device 1 may also be connected to a tube (not shown) from a blood bag or similar container without any needles involved. That is, the sampling device or adapter 1 is typically used by a doctor, researcher, healthcare worker, medical technician or the like to allow that person to collect samples of blood or body fluid either directly from a patient using venipuncture or directly from blood bags or similar containers. The needle 200 is often a fixed size of heavy gauge. The needle on the external end of the tube barrel holders may vary in gauze/size depending upon the patient.

Figure 5A:
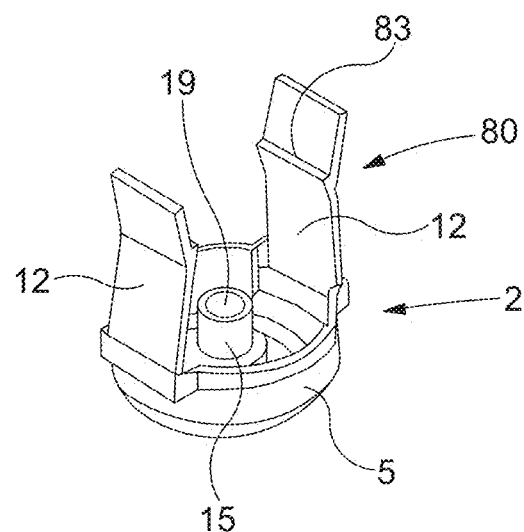
FIGS. 5a, 5b, 5c, 5d and 5e are perspective, cross-section along W-W, side and end views of the base of FIG. 1.
Figure 5B:
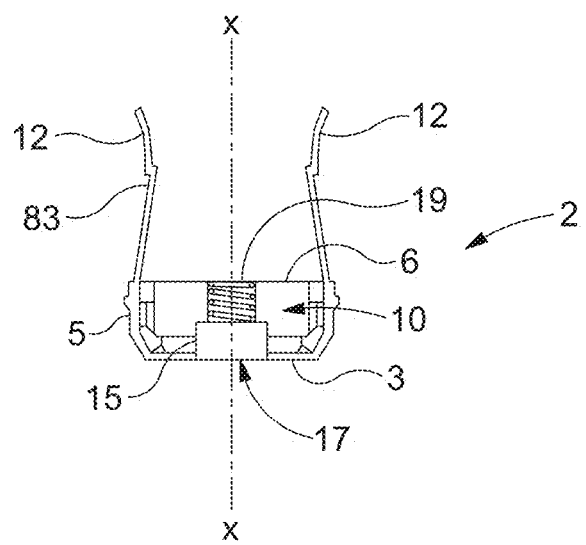
Figure 5C:
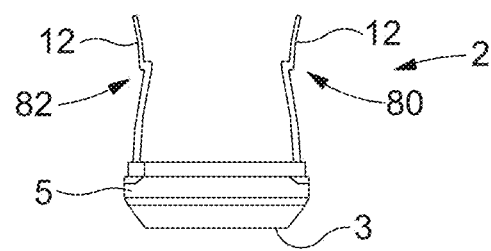
Figure 5D:
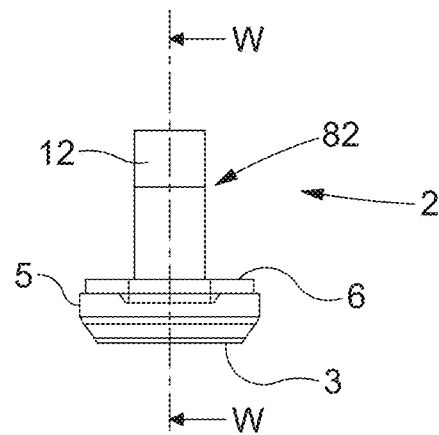
Figure 5E:
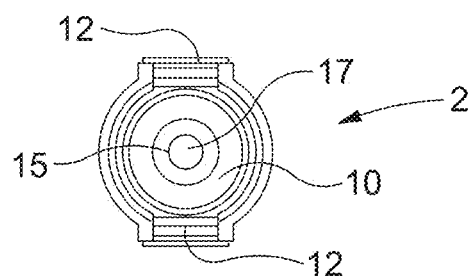

The device 1 as best seen in FIGS. 5a to 5e includes a base 2 having a bottom end 3, a side wall 5 extending away from the bottom end 3 and towards a rim 6 to define a base chamber 10. In a preferred form, the base 2 is generally circular. However, it should be noted that there are other shapes such as squares, rectangles, or triangles that could also be utilised. A pair of elongate flexible arms 12 extend upwardly from the side wall 5 and bottom end 3. It should be noted that though the pair of flexible arms 12 are shown, more than two arms 12 could be utilised. The arms 12 are typically oppositely located across the base chamber 10. An elongate boss 15 is located within the base chamber 10 and extends away from the bottom end 3. The boss 15 includes two steps in a preferred form and as best seen in FIG. 5b. It could however include many steps or only a single step. The boss 15 has an aperture 17 therethrough and as there are steps shown, the boss 15 has two different diameters. The aperture 17 could be the same diameter or different diameters within the boss 15. The aperture 17 defines a longitudinal axis XX. A portion or section 19 of the aperture 17 in the boss 15 could be a connecting section and include a thread or the like as shown in FIG. 5b to correspond with a connecting section on a connector inserted thereto. The connecting section though could include other fastening means such as bonding by an adhesive or the like. The device 1 further includes a spring 20 adapted in use to be located at least partly within the base chamber 10 about the boss 15 and extending away from the bottom end 3. A collar 29 extends from the bottom end 3 to retain or at least limit movement of the spring 20.

A lower member 25 is best seen in FIGS. 7a to 7e and has a flange 27, an aperture 28 adapted in use to surround the axis XX and a collar 30 extending away from the flange 27 and adapted to retain or at least limit movement of an end of the spring 20. At least one or more legs 32 extend away from the flange 27 away from the collar 30. In the embodiments shown, there are four legs 32, however any number of legs 32 could be utilised. The collar 30 is shown to be circular along with the flange 27. However, they could be other shapes. In the embodiment shown, each leg 32 has a locking protrusion 33.

Figure 6A:
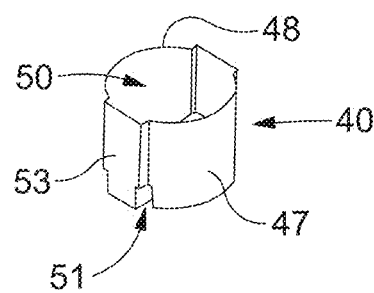
FIGS. 6a, 6b, 6c and 6d are perspective, cross-section along V-V, end and side views of the upper member of an embodiment of the present invention.
Figure 6B:
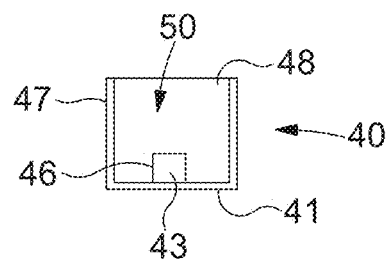
Figure 6C:
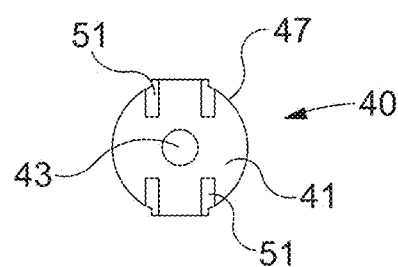
Figure 6D:
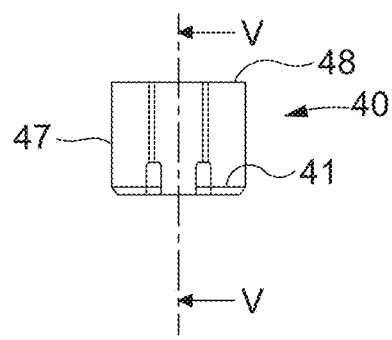
Figure 7A:
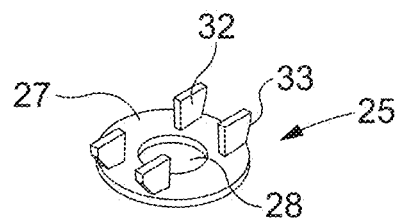
FIGS. 7a, 7b, 7c and 7d are perspective, cross-section along P-P, end and side views of the lower member of an embodiment of the present invention.
Figure 7B:
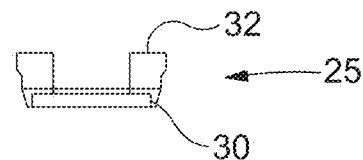
Figure 7C:
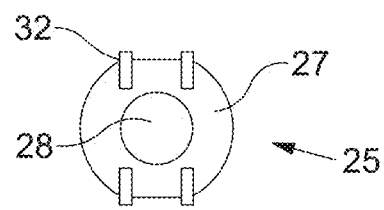
Figure 7D:
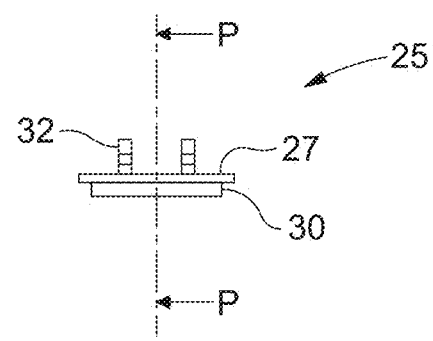

As best seen in FIGS. 6a to 6d, there is shown an upper member 40 which has a separate flange 41 which in use is operatively associated with the flange 27 of the lower member 25. The upper member 40 acts as a safety shield to prevent accidental needle exposure. An aperture 43 is also located within the flange 41 which also corresponds to the aperture 28 of the lower member 25. A boss 46 extends about that aperture 43 and away from the flange 41. A wall 47 extends away from the flange 41 to a rim 48 to define a sampling chamber 50. At least one slot 51 is provided in the flange 41 (as best seen in FIG. 6c) and adapted in use to receive at least one leg 32 of the lower member 25 in use. In the preferred embodiment there are four legs 32 and four slots 51. The wall 47 can include a guide, protrusion or other shaped part 53.

Figure 3:
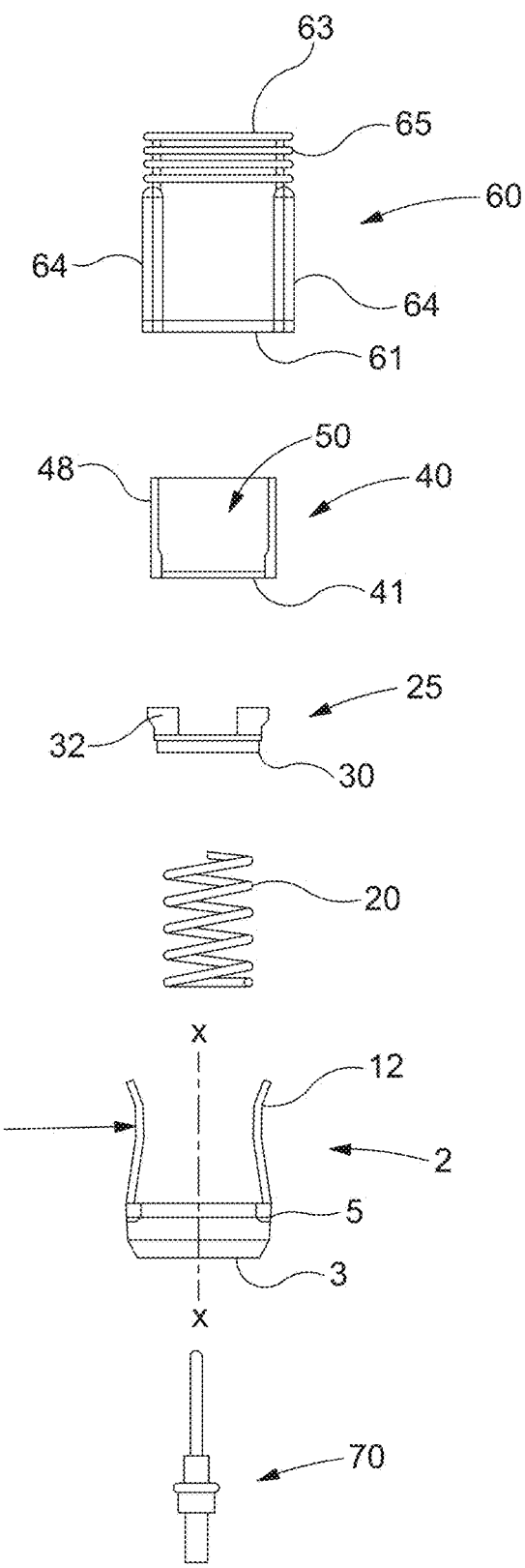
FIG. 3 is an exploded components view of FIG. 1.
Figure 4A:
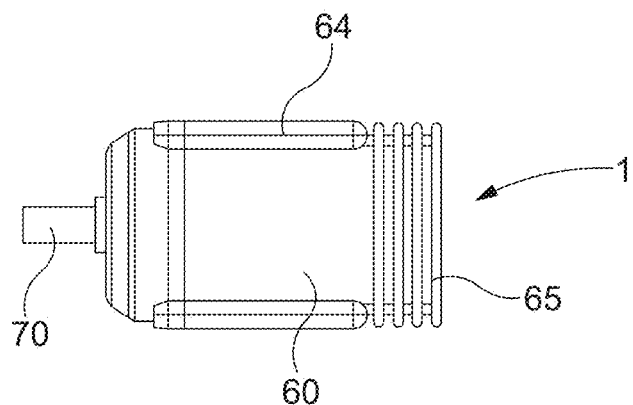
FIGS. 4a to 4c are side, end and cross-section along T-T views of an embodiment of the present invention.
Figure 4B:
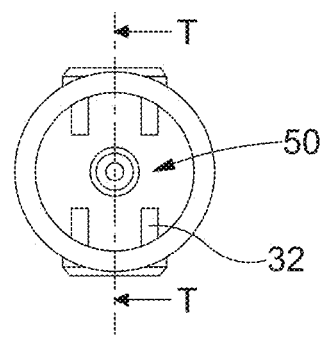
Figure 4C:
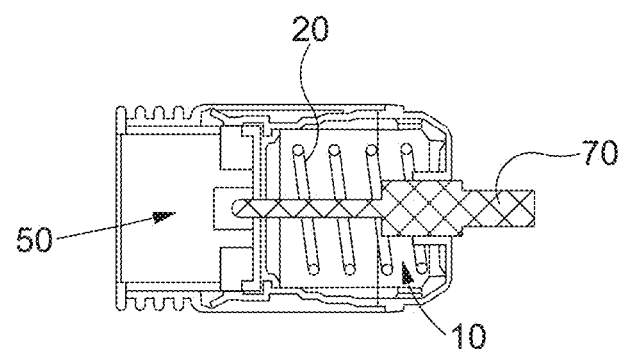

The device 1 as best seen in FIG. 3 further includes an elongated cover 60 having a first end 61 and a second end 62. The first end 61 is adapted in use to connect with the base 2 and the second end 62 is adapted in use to connect with the upper member 40. The cover 60 having shaped guides, protrusions, parts 64 corresponding to parts 53 of the wall 47 to provide snap locking engagement or other such locking arrangements. The cover 60 may also include threaded sections 65 for connection to various containers or the like.

A connector 70 as best seen in FIG. 2 is operatively associated with the boss 15 and the base 2 and has an elongated tube therethrough adapted to extend along the axis XX receive a needle and at the other end has suitable features to connect to a blood bag tubing, needles, luer needles or the like. Although commonly the connector 70 would take the form of a luer, it is also possible to have an assembly that does not include a luer taper but simply has a tube, connector or the like.

In the art of blood collecting a typical "tube-barrel holder" or also sometimes called "multi-sampling port" is used. It may also have a lid at the open end. The base typically has a boss with a female thread. Also used is the multi sample luer adaptor which consists of a plastic connector into which a steel needle is bonded and the needle is then covered with an elastomeric sheath. The sheath allows multiple sampling of the blood via the needle using different test or evacuated tubes. The sheath retracts over the open needle mouth when the test tube is retracted thus stopping flow of blood until another tube is inserted. Basically the sheath works like a valve. The needle in the sheath is normally a fixed size and does not vary with patients. The sheathed needle is always connected inside the tube barrel holder. The blunt end of the multi-sample luer adaptor is often tapered (hence called a luer) to connect to connectors with corresponding tapers. If a connection to a tube is required instead, then there may not be any taper on this end (and it will not be called a luer connector).

Often a "winged-needle" also called "butterfly" needle is used and connected via a tubing to a female luer connector. This luer connector can be connected to the male luer of the "multi-sample luer adaptor" mentioned above. The winged needle comes in various sizes. The multi sample luer adaptor for example can be screwed into the base of a tube-barrel holder. The winged needle is then used in a patients arm to extract blood. Sometimes instead of using "winged needles", medical staff use a double needle assembly which has a sheathed needle connected to a longer hollow needle (that has no sheath). This can be screwed into a tube barrel holder and used to collect blood from patients as well. The sheath needle is screwed inside the tube barrel holder and the venipuncture needle is outside. The exposed needle comes in various sizes (gauge 20G, 21G, 22G etc). The sheathed needle is a fixed size and does not change. It is generally a heavier gauge so that it can penetrate elastomeric bungs or plugs.

Sometimes needles with a female luer are directly connected to the male luer of the "multi sample luer adaptor" which allows the tube barrel holder to be connected to a needle for venipuncture of patient. When venipuncture into an arm with a needle the blood collects into an evacuated tube. The evacuated tube is fully inserted into the tube barrel holder so that the sheathed needle inside the tube barrel holder has penetrated the bung in the evacuated tube and thus allows the flow of blood from the vein into the tube. Sometimes the tube barrel holder can be connected to a "cannula" which is inserted into a vein. The tube barrel holder can be connected directly to tubing in a blood bag kit. In these situations the tube barrel holder is used to get blood samples from the bag and not directly from a patient's arm. Inside the tube barrel holder is the sheathed needle or multisample adaptor. The evacuated tubes or test tubes have a slight vacuum which allows blood to be "sucked" into the chamber and they come in various sizes generally 3 ml to 10 ml. In all cases the tube barrel holder must contain a multi sample needle (sheathed needle) which may be; connected to a second needle via a luer connection. Second needle can be normal or butterfly type; connected directly to a second needle with no luer connection; or connected directly to a tube from a blood bag with no luer connection.

Turning to in use of the present invention now, the upper and lower members 40, 25 are adapted to move along the axis XX by positioning of a sampling container 201 in said sampling chamber 50 and the application of a force by a user downwardly towards said base 2. This will result in the device 1 looking like FIG. 9. Upon movement of said upper member 40, the end 72 of said connector 70 extends beyond said boss 46 of said upper member 40 permitting a needle 200, tube or the like located within said connector 70 to discharge liquid into said sampling container 201 located in said sampling chamber 50 without needles 200 sticking a user or transference of matter.

Figure 8:
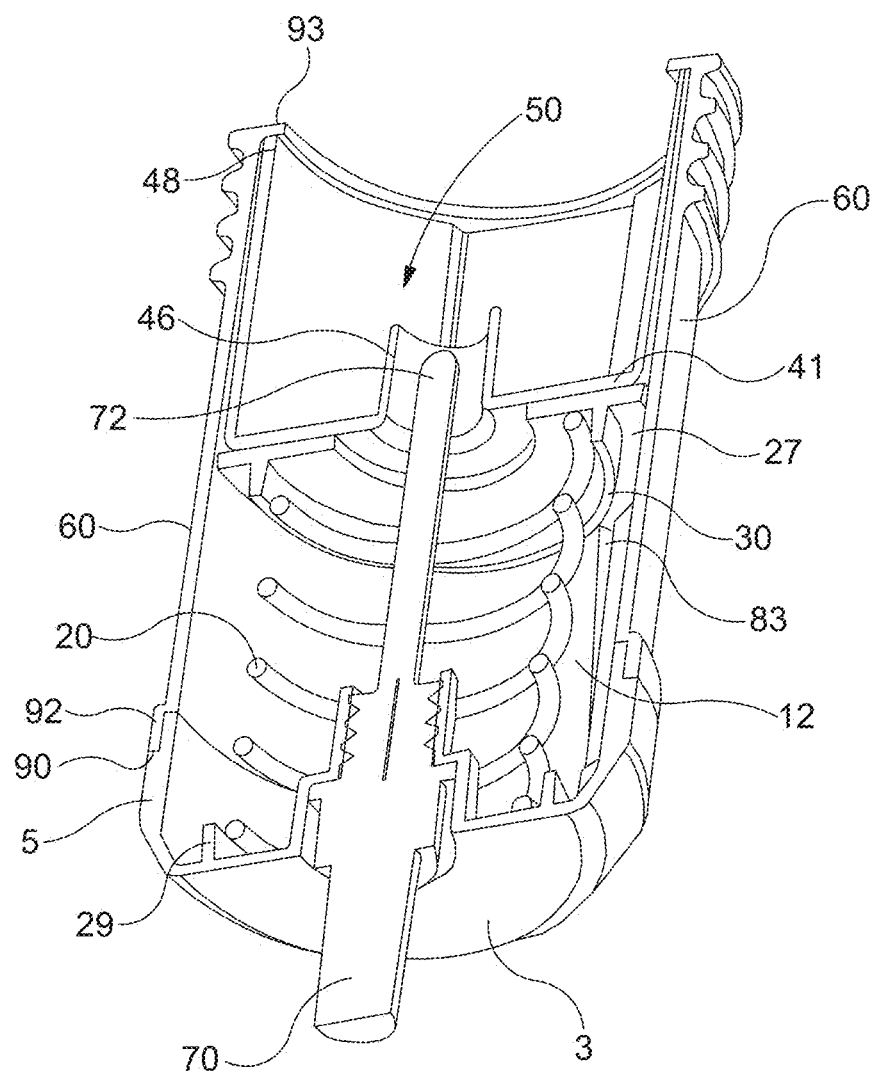
FIG. 8 is a rotated cross-sectional view of FIG. 2.

In a preferred form and as best seen in FIGS. 5a and 5b and 8, the arms 12 of the base 2 have locking means or member 80 adapted to engage and disengage the lower member 25 in use to permit movement of said upper and lower members 40, 25 along the axis XX. Typically the locking means 80 includes a flexible portion 82 of the arms 12 that includes a step 83. The step 83 is adapted to contact the flange 27 of said lower member 25. Upon application of said force, said flange 27 and said step 83 are moved out of engagement with the lower member 25 and towards the cover 60.

In a preferred form, the rim 6 of the base 2 also includes a step 90 adapted in use to connect with a corresponding step 92 in the first end 61 of the cover 60 as best seen in FIGS. 8 and 9. The second end 62 of the cover 60 includes a lip 93 extending towards the axis XX and adapted to connect with the rim 48 of said upper member 40.

Another variation of the present invention has the upper member 40 and lower member 25 combined. The legs 32 in the lower member 25 will then be the flexible arms 12 instead, and can be depressed.

Another variation of the present invention does not have the boss 46 but the device 1 is longer so that the tip 72 of the connector 70 (in some forms a sheathed needle) is below the opening or orifice or lip 93.

Figure 11:
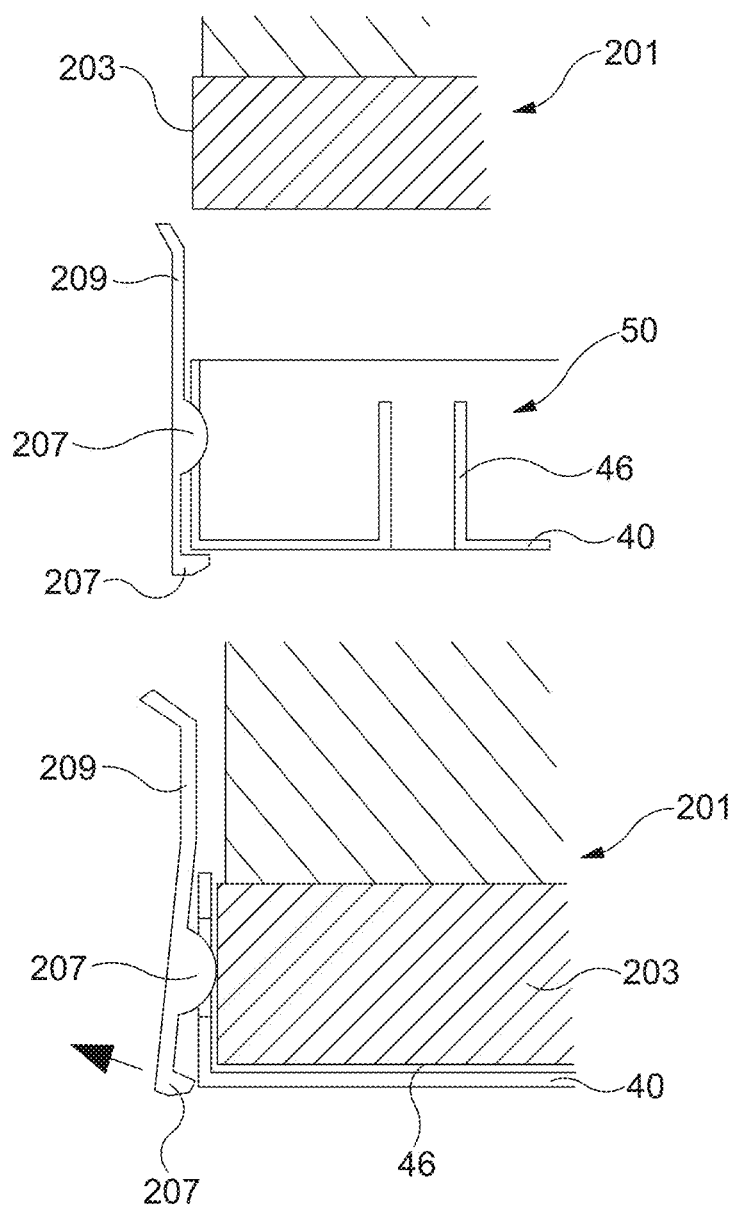
FIG. 11 are partial views showing the connecting of parts.
Figure 12:
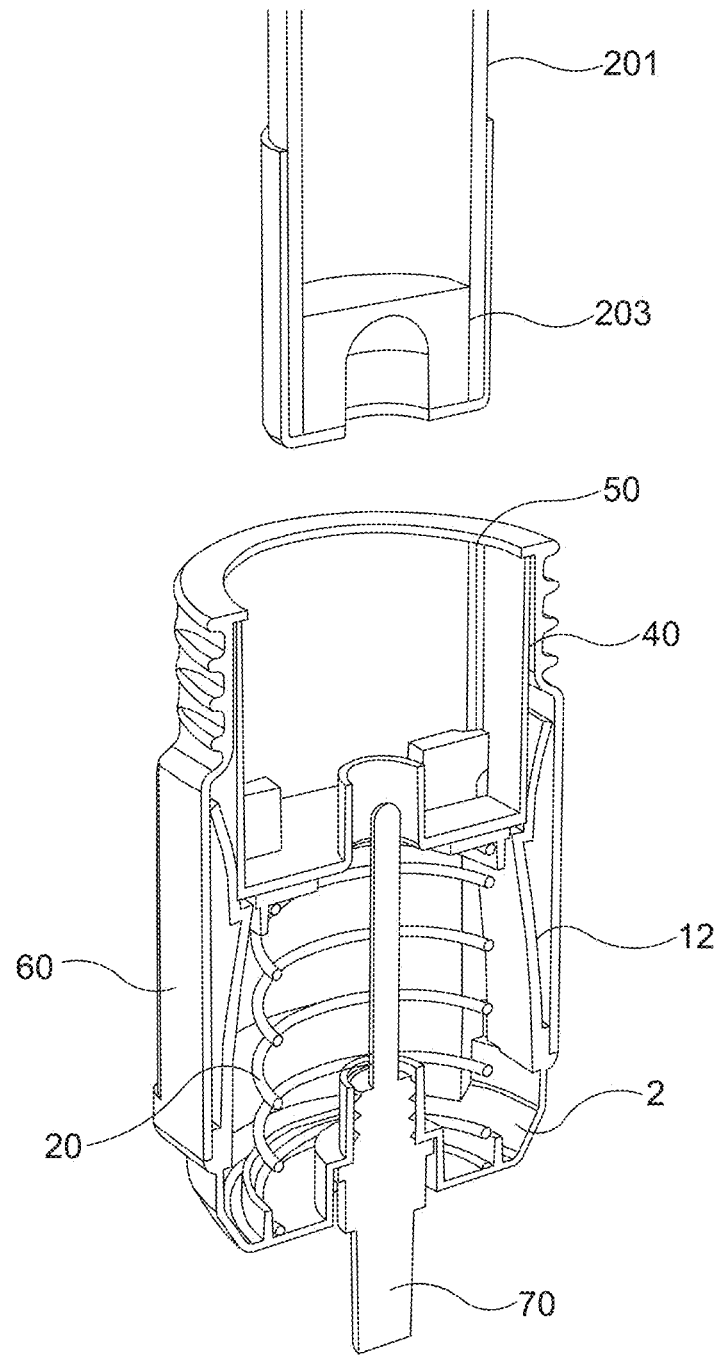
FIG. 12 shows a cross sectional view of the invention in operation.
Figure 13:
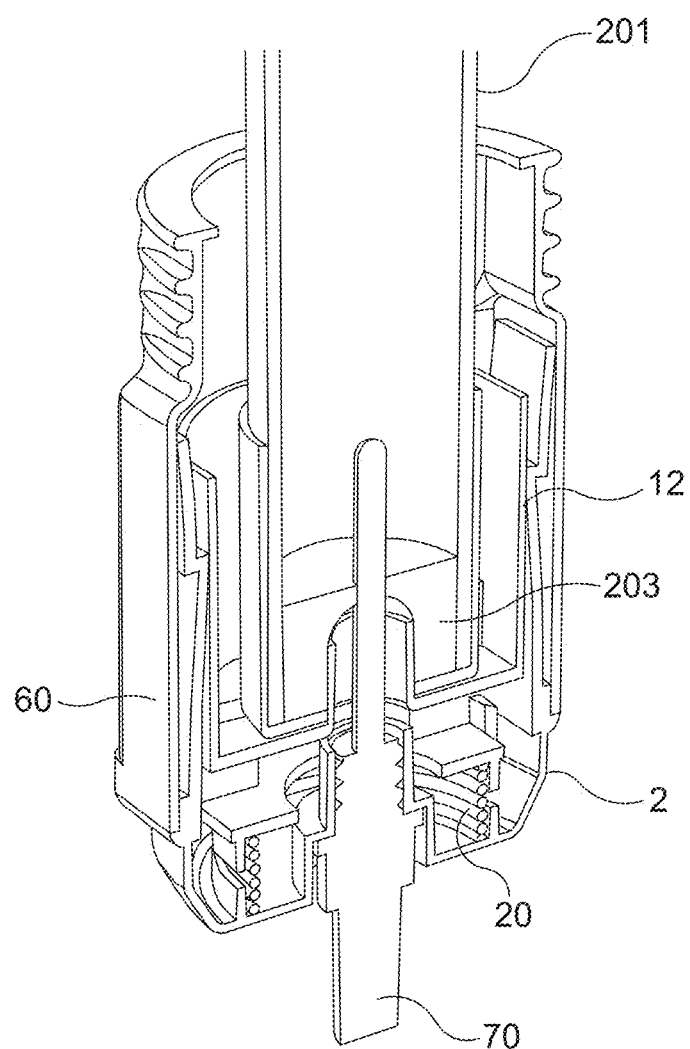
FIG. 13 shows another cross sectional view of the invention in operation.

In yet another embodiment of the device 1, the upper member 40 has retaining arms 209 that retain the lower member 25, and the lower member 25 acts as a safety shield against needle stick injury by shielding the needle 200. The retaining arms 209 would be flexible and can flex radially outwards from the centre axis of the device 1, and have humps or protrusions 207 on each arm 209 as seen in FIG. 11. The lower member 25 would have openings in the wall co-located with the retaining arms 209 of the upper member 40 and allowing the humps or protrusions 207 in the arms 209 to penetrate the lower member 25 through the openings. The protrusions are designed to interact with the appropriate receiving container 201 when it is inserted into the chamber 50 of the device 1 and to flex radially outward (away from the centre line of the device along axis XX). This radial movement away allows the lower member 25 to be released and move down towards a needle assembly and/or base 2.

In yet another embodiment of the device 1, the upper member 40 has flexible arms 209 that retain the lower member 25, and the lower member 25 acts as a safety shield against needle stick injury by shielding a needle 200. The lower member 25 has flexible arms that have protrusions or humps that face inwards and which are co-located with flexible arms 209 of the upper member 40. When a receiving container 201 is inserted into the device 1, it pushes the protrusions in the arms of the lower member 25, which in turn push radially outwards the flexible retaining arms 209 of the upper member 40. This movement of the retaining arms 209 releases the lower member 25, which can then move down towards a needle assembly and/or base 2.

Another variation of the device 1 does not have any spring 20 in the device 1, but has appropriate features on the upper and lower members 40, 25 to allow the receiving container to engage with these members 40, 25 so that the members 40, 25 are returned to the original position by the action of removing the receiving container from the chamber 50 without the need for a spring 20 or similar mechanism.

In the first preferred embodiment, in the locked state, the upper member 40 acts as a safety shield against needle stick injury as the steps 80 in legs 12 of base 2 prevent the upper and lower members 40, 25 from being able to move down towards the needle assembly and/or base 2. However, when a receiving container 201 with the correct dimensions is inserted into the chamber 50 of the device 1 and pushed against the legs 32 of lower member 25, this causes the lower member 25 to move down towards the needle 200 and base 2 whereby the legs 32 push the arms 12 radially outwards. This outward movement of arms 12 causes the upper member 40 to become un-locked and hence able to move down over the needle 200. The spring 20 acts to keep the upper member 40 in the locked state when not in use.

Steps for engagement and disengagement of the receiving container (generally a test tube or other similar container) 201, typically include the receiving container (for example a test tube) as it is cylindrical in shape and is sealed on one end and has an elastomeric bung or stopper 203 (see FIG. 10) on the other end. The receiving container 201 may be evacuated so as to have a lower pressure than atmospheric to allow the liquid to be "sucked" into the receiving container. The elastomeric bung 203 in the receiving container 201 is designed to be pierced by a needle 200 during transfer of liquid and automatically reseals when the needle 200 is retracted from the bung 203. In most cases, as the sheathed needle enters the bung, the sheath retracts and does not penetrate the bung, only the steel needle penetrates the bung. The connector 70 of the device 1 is connected to a discharging container (for example a blood bag, arm of a patient or similar) via a suitable tubing or through a needle, cannula or other connectors like a blunt tip cannula. To transfer liquid from the discharging container. The receiving container 201 is inserted into the chamber 50 of the device 1. In the first embodiment of the device 1, the legs 32 of the lower member 25 are pushed down when the receiving container is pushed towards the needle assembly (connector 70). The legs by moving down cause the arms 12 to flex radially outwards away from the axis XX, which thereby releases the upper and lower members 40, 25 allowing both to move down over the sheathed needle and compressing the spring 20 in the process. The needle enters through the boss 15 in the lower member 25 and pierces the sheath 205 and the elastomeric stopper 203 of the receiving container 201 and when fully penetrating the bung 203 inside the receiving container 201 allows the liquid to flow from the discharging container (not shown) into the receiving container 201 via the connector 70 and the needle 200 inserted therein. When the required amount of liquid has been transferred into the receiving container, the receiving container is retracted out from the device 1. This causes the spring 20 to extend and push the lower and upper members 25, 40 back over the needle 200 and into the locked position and into the locked or retained position by the arms 12. Simultaneously the elastomeric sheath 205 retracts back over the needle 200 and seals the open end of the connector 70 thus stopping the flow of any further liquid until, if required, another receiving container 201 is inserted into the device 1 and the process repeated.

In the second embodiment of the device 1 as best seen in FIG. 11, the insertion of the receiving container 201 into the device chamber 50 causes the humps 207 on the legs 209 of the upper member 40 to be pushed radially outwards. This releases the lower member 25 holding the upper member 40 and allows the receiving container 201 to move down over the sheathed needle 200. When the needle 200 fully penetrates the bung 203, it allows the liquid to transfer from the discharging container to the receiving container 201. After the desired amount of liquid has been transferred, the receiving container 201 is retracted from the device 1. This allows the spring 20 to extend and push the lower member 25 back over the sheathed needle 200 and into the position where it is entrapped by the flexible retaining arms of the upper member 40.

In the third embodiment of the device, the insertion of the receiving container 201 into the device chamber 50 causes the humps on the legs of the lower member 25 to be pushed radially outwards. This causes the retaining arms on the upper member 40 to be push out radially thus releasing the lower member 25 and allowing the receiving container to move down over the sheathed needle 200. When the needle 200 fully penetrates the bung 203, it allows the liquid to transfer from the discharging container to the receiving container 201. After the desired amount of liquid has been transferred, the receiving container 201 is retracted from the device 1. This allows the spring 20 to extend and push the lower member 25 back over the needle 200 and into the position where it is entrapped by the flexible retaining arms of the upper member 40.

The device 1 in a preferred form is used for evacuated tubes for transferring blood or its components into the tubes. The device 1 has a safety shield (upper member 40) that prevents needle stick injury from the sheathed needle 200 that is located in the device 1 in use. When the tube 201 is inserted into the device 1 by a user it disengages the safety shield 40 and allows the sample to be collected. The locking mechanism 80 is designed to be difficult to disarm by a person sticking his or her finger in the device 1. The raised section (boss) 46 around the needle 200 in the safety shield (upper member 40) is part of the design to prevent easy disarming of the shield.

Although the invention has been described with reference to specific examples, it will be appreciated by those skilled in the art that the invention may be embodied in many other forms.

What is claimed is:

1. A sampling device adapted to connect in use a needle or blood bag tube with a sampling container; said device including
   a base having a bottom end, a side wall extending away from said bottom end to a rim to define a base chamber, a pair of elongate flexible arms extending from said side wall away from said bottom end, said arms being oppositely located across said base chamber, an elongate boss located within said base chamber and extending away from said bottom end, said boss having an aperture defining a longitudinal axis;
   a spring adapted in use to be located at least partly within said chamber, about said boss and extending away from said bottom end;
   a lower member having a flange and an aperture, a collar extending from said flange and adapted to retain an end of said spring, and at least one leg extending away from said flange opposite to said collar;
   an upper member having a flange in use operatively associated with the flange of said lower member, said flange having an aperture corresponding with said aperture of said lower member, a boss extending about said aperture and away from said flange, a wall extending away from said flange to a rim to define a sampling chamber; at least one slot adapted in use to receive the at least one leg of said lower member in use;
   an elongate cover having a first end and a second end, said first end being adapted in use to connect to said base and said second end being adapted in use to connect to said upper member;
   a connector operatively associated with said boss of said base and having an elongate tube adapted to extend along said axis;
   whereby in use, said upper and lower members are adapted to move along said axis by the positioning of a sampling container in said sampling chamber and the application of a force towards said base, upon movement of said upper member, an end of said tube of said connector extends beyond said boss of said upper member permitting a needle or blood bag tube located within said connector to discharge liquid into said sampling container.

2. The sampling device according to claim 1, wherein said arms of said base have a locking member adapted to engage and disengage said lower member in use to permit movement of said upper and lower members along said axis.

3. The sampling device according to claim 2, wherein said locking member includes a flexible portion having a step, the step adapted to contact said flange of said lower member, upon application of said force said step being moved out of engagement with said lower member and towards said cover.

4. The sampling device according to claim 1, wherein said boss of said base includes a connecting section, at least a portion of said connector having a corresponding connecting section to secure said connector to said boss.

5. The sampling device according to claim 4, wherein said connecting sections include threads.

6. The sampling device according to claim 1, wherein said connector includes a luer.

7. The sampling device according to claim 1, wherein said base includes a retainer extending from said bottom end and adapted to retain an end of said spring.

8. The sampling device according to claim 1, wherein said lower member includes four legs and said upper member includes four corresponding apertures.

9. The sampling device according to claim 1, wherein said rim of said base includes a step adapted in use to connect with a corresponding step in said first end of said cover.

10. The sampling device according to claim 1, wherein said second end of said cover includes a lip extending towards said axis and adapted to connect with said rim of said upper member.

\* \* \* \* \*

UNITED STATES PATENT AND TRADEMARK OFFICE
CERTIFICATE OF CORRECTION

| | | |
|---|---|---|
| PATENT NO. | : 9,962,116 B2 | Page 1 of 1 |
| APPLICATION NO. | : 14/877760 | |
| DATED | : May 8, 2018 | |
| INVENTOR(S) | : Avtar Kashmirian | |

It is certified that error appears in the above-identified patent and that said Letters Patent is hereby corrected as shown below:

On the Title Page

Item (54) and in the Specification, Column 1, Line 1, Title: Please delete "SAMPLING DEVICE" and replace with --A SAMPLING DEVICE--

Signed and Sealed this
Twenty-fourth Day of July, 2018

Andrei Iancu
*Director of the United States Patent and Trademark Office*